United States Patent [19]

Guyton

[11] 4,029,113

[45] June 14, 1977

[54] WAXED DENTAL TEXTILE MATERIAL AND METHOD OF PREPARING AND USING THE SAME

[76] Inventor: William Cecil Guyton, 922 Porter Ave., Ocean Springs, Mich. 39564

[22] Filed: Feb. 20, 1975

[21] Appl. No.: 551,417

[52] U.S. Cl. ............................................. 132/91
[51] Int. Cl.² ....................................... A61C 15/00
[58] Field of Search .................. 132/91, 92 R, 92 A

[56] References Cited

UNITED STATES PATENTS

| | | | |
|---|---|---|---|
| 2,667,443 | 1/1919 | Ashton | 132/91 |
| 3,830,246 | 8/1974 | Gillings | 132/89 |

*Primary Examiner*—G.E. McNeill

*Attorney, Agent, or Firm*—L. S. Van Landingham, Jr.

[57] ABSTRACT

Waxed dental textile material is provided which has a fluorine compound distributed through the wax coating. The fluorine compound provides fluoride ion in a therapeutic amount to inhibit the formation of dental caries when the waxed dental textile material is intimately contacted with the teeth and gingiva to remove food deposits. A method of preparing the dental textile material is provided which assures that a proper amount of fluorine compound is substantially uniformly distributed through the wax coating. A method of inhibiting the formation of dental caries is also provided wherein the waxed dental textile material of the invention is used periodically to remove food deposits from the teeth and gingiva.

12 Claims, 1 Drawing Figure

U.S. Patent
June 14, 1977
4,029,113
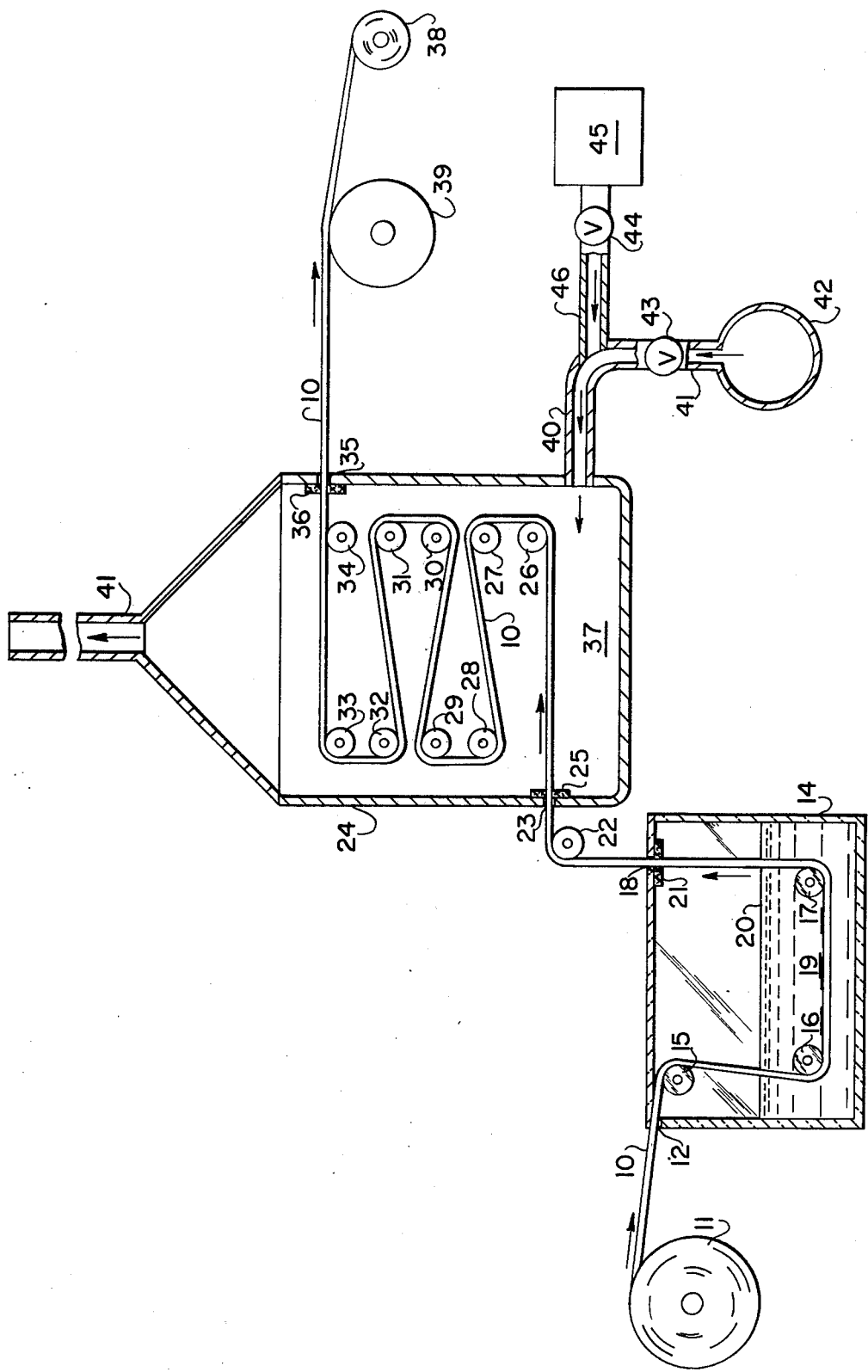

WAXED DENTAL TEXTILE MATERIAL AND METHOD OF PREPARING AND USING THE SAME

THE BACKGROUND OF THE INVENTION

1 The Field of the Invention

The present invention broadly relates to waxed dental textile materials. In one of its more specific variants, the invention is concerned with the application of a fluorine-containing wax coating to dental textile materials which provides fluoride ion to inhibit the formation of dental caries. The invention further relates to the waxed dental textile material of the invention and the use thereof in inhibiting the formation of dental caries.

2 The Prior Art

Bacterial action on food deposits tends to cause disintegration and erosion of the dental surfaces and soreness and softening of the gums. This is especially pronounced in the more susceptible decay and inflammation areas such as the contact points of the teeth and at or immediately below the gingiva. Dental caries are one result of such bacterial action, and inflammation of the gingiva in another.

Dental aids such as floss and tape have been used extensively heretofore for periodically removing food deposits from the teeth and gingiva. The prior art dental floss and tape may be waxed or unwaxed, and it may be prepared from multi-strand textile materials such as nylon or cotton. However, the prior art waxed dental floss or tape was not provided with an entirely satisfactory wax coating which contained a substance effective to inhibit the formation of dental caries. As a result, while the prior art dental floss and tape performed the basic function of removing existing food deposits, it was not capable of preventing future food deposits from causing dental caries through fermentation and bacterial action prior to removal. Thus, the dental art has long sought an entirely satisfactory waxed dental tape which is capable of not only removing food deposits from teeth and the gingiva, but which is also capable of effectively inhibiting the tendency toward future formation of dental caries.

THE SUMMARY OF THE INVENTION

The present invention provides an improved waxed dental textile material which has the important additional benefit of inhibiting the formation of caries in the cleaned teeth, and especially at the most susceptible decay areas such as the contact points and near or beneath the gingiva. This is accomplished by providing a wax coating which releases fluoride ion in an amount effective to inhibit the formation of dental caries when the waxed dental textile material is intimately contacted with the teeth and gingiva to remove food deposits. The improved waxed dental textile material is preferably prepared by the novel method of the invention. The resultant waxed dental textile material is especially useful in the novel method of the invention for inhibiting the formation of dental caries in teeth.

The following detailed description of the invention, including the preferred variants and embodiments thereof, may be referred to for a more complete and comprehensive understanding of the invention.

BRIEF DESCRIPTION OF THE DRAWING

The single FIGURE of the drawing schematially illustrates one presently preferred arrangement of apparatus for applying a fluorine-containing wax coating to dental textile material.

THE DETAILED DESCRIPTION OF THE INVENTION INCLUDING CERTAIN PRESENTLY PREFERRED VARIANTS AND EMBODIMENTS THEREOF

Referring now to the drawing, a dental textile material 10 is fed from a master supply spool 11 through an opening 12 into tank 14. The textile material 10 then passes over roll 15 and downward under rolls 16 and 17 before being withdrawn upward from tank 14 via opening 18. The tank 14 is partially filled with a wax-containing liquid 19 which contains a fluorine compound to be described more fully hereinafter. The rolls 16 and 17 are submerged in the liquid 19, and thus the textile material 10 is saturated therewith upon emerging from the liquid surface 20.

Excess liquid 19 is removed from the textile material 10 by felt wiper 21, and then the textile material which is saturated with the wax-containing liquid 19 is passed over roll 22 and through opening 23 into dryer-cooler 24. The opening 23 is provided with felt washer 25 to prevent excessive loss of the gaseous treating fluid from the interior 37 of dryer-cooler 24. The gaseous treating fluid may be, for example, either hot air or cool air. The textile material 10 is then passed through dryer-cooler 24 along a circuitous path defined by the arrangement of rollers, 26, 27, 28, 29 30, 31, 32, 33, and 34, and it is then withdrawn from dryer-cooler 24 through opening 35. The felt washer 36 prevents excessive loss of the gaseous treating medium from the interior 37 of dryer-cooler 24. After passing through opening 35, the textile material 10 has a solid wax coating thereon and may be wound on consumer spools 38 or packaged in other suitable consumer dispensers in lengths controlled by photoelectric counting or measuring device 39.

The hot or cool gaseous treating medium is supplied to the interior 37 of dryer-cooler 24 via conduit 40, and after passing upward in intimate contact with the textile material 10 to be treated, is then withdrawn via conduit 41. In instances where it is desired to evaporate a volatile ingredient from the liquid 19 saturating textile material 10, then a hot gaseous treating medium is supplied to interior 37 by heater-blower 42 via conduit 40 upon opening valve 43 and closing valve 44. In instances where the liquid 19 is a molten normally solid substance such as wax at an elevated temperature and thus must be cooled to solidify the same, then valve 43 is closed, valve 44 is opened, and a cool gaseous treating medium is supplied to interior 37 by cooler-blower 45 via conduits 46 and 40.

The supply spool 11 is preferably spring loaded for tension purposes, and the consumer spool 38 is preferably provided with prior art means not shown for rotating the same and thereby pulling the textile material 10 through tank 14 and dryer-cooler 24. The tension means for roll 11 and the driving means for roll 38 may be of conventional construction and design and are not shown in the interests of clarity and simplifying the drawing. The counter 39 likewise may be of conventional construction and design, and performs the function of allowing a predetermined length or amount of treated textile material 10 to be supplied to a plurality of sequentially positioned consumer spools 38 or other suitable consumer dispensers.

The textile material 10 may be any suitable prior art dental textile material but is preferably unwaxed, of indefinite length, and composed of a plurality of elongated generally longitudinally extending textile fibers. Suitable materials for use in preparing the textile material 10 include naturally occurring textile fibers, such as cotton and flax, and synthetic textile fibers such as nylon and other polyamides, the polyesters and the like. Cotton is usually the preferred naturally occurring textile fiber, and nylon is usually the preferred synthetic textile fiber. In all instances, it is usually preferred that the textile material 10 be composed of a plurality of individual generally longitudinally extending textile fibers. The textile fibers may be relatively short such as cotton fibers or continuous strands or filaments such as with nylon. Such plurality of fibers or multi-strands may be loosely twisted so as to assume a semi-thread to thread-like configuration. The dental textile material 10 may be conventional dental floss. As a general rule, dental floss or tape prepared from a plurality of continuous nylon filaments or strands is preferred.

The tank 14, the dryer-cooler 24 and the rolls 16, 17, 22 and 26-34 may be constructed of prior art materials which are non-corrosive in liquid 19 and the gaseous treating medium in interior 37. For instance, the tank 14 may be glass lined and glass coated steel rolls 16, 17, 22 and 26-34 may be employed.

The liquid 19 may be, for example, a solution of wax in a volatile solvent, or an aqueous emulsion of wax, or molten wax. In instances where the liquid 19 is molten wax, or when it is preferred that a solution or aqueous emulsion of wax be applied at an elevated temperature, then prior art heating means which are not shown in the interest of clarity and simplifying the drawing may be provided in tank 14.

The wax in liquid 19 may be any suitable wax or wax-like substance which is applied to dental textile materials as a waxing agent. Such substances, including those specifically mentioned hereinafter, may be referred to collectively in the specification and claims as "wax" and the resulting product "waxed" dental textile material in the interest of simplifying the discussion and claims. The wax may be naturally occurring and/or it may be a synthetic wax or waxy substance. Specific examples of mineral waxes include microcrystalline wax, paraffin wax, and other waxes derived from petroleum, ozocerite, Montan and ceresin. Animal waxes include spermaceti, beeswax, stearic acid and Chinese wax. Vegetable waxes include carnauba, Japan wax, Bayberry and candelilla. Synthetic waxes include polyethylene, polypropylene, polyethylene glycol, polyoxyethylene esters, chloronaphtalenes, the sorbitols and chlorotrifluoroethylene resins.

In instances where the liquid 19 is a solution, then the solvent may be any suitable volatile solvent for the specific wax which is selected. Examples of organic solvents which are generaly useful include The liquid aliphatic or aromatic hydrocarbons and especially petroleum distillates such as kerosene, gasoline, diesel oil, gas oil, benzene and toluene, and liquid aliphatic or aromatic chlorinated hydrocarbons, esters and ketones and especially those containing 1-5 carbon atoms. The aliphatic hydrocarbons or chlorinated aliphatic hydrocarbons may have a linear or branched chain configuration. It is only necessary that the solvent be liquid at the temperature existing in tank 14 and capable of being removed by evaporation at the temperature existing within dryer-cooler 24. However, normally liquid volatile solvents are usually preferred.

In instances where liquid 19 is an aqueous wax emulsion, then the wax emulsion may be prepared in accordance with prior art practices. Suitable emulsifying agents include the alkali metal salts of fatty acids, synthetic nonionic surfactants and anionic surfactants. As a general rule, the emulsion may be prepared by agitating the wax in the molten state with approximately 1-10 and preferably 1-4 volumes of water in the presence of about 1-10% by weight of the emulsifying agent based upon the weight of the wax under vigorous conditions of agitation.

In instances where the liquid 19 is molten wax, then for best results the selected wax should be readily liquifiable and fluid at a relatively low elevated temperature such as about 150°-450° F. Examples of waxes which may be liquified at relatively low elevated temperatures include microcrystalline wax, paraffin wax and similar mineral, animal and vegetable waxes.

The wax coating which is applied to the dental textile material 10 contains the fluorine compound distributed therein substantially uniformly, and in a therapeutic amount to provide sufficient fluoride ion to inhibit the formation of dental caries when the waxed dental textile material is intimately contacted with the teeth and gingiva to remove food deposits. While the concentration of the fluorine compound may vary over wide ranges, usually it is present in an amount to provide about 0.0001-2% by weight of fluoride ion and preferably in an amount to provide about 1-1.5% by weight of fluoride ion. The best results are usually achieved at a concentration which provides approximately 1.25% by weight of fluoride ion. In instances where the liquid 19 is a molten wax which is applied directly to the textile material 10 and then solidified, then it may contain the fluorine-containing compound in the concentrations give above for the wax coating.

When the liquid 19 is an aqueous emulsion, gel-like or a solution of the wax, then preferably the fluorine compound is present in liquid 19 in an amount to provide about 0.001-10% by weight of fluoride ion and preferably about 0.01-5% by weight of fluorine ion based upon the weight of the liquid 19. The best results are usually achieved when the fluorine compound is present in liquid 19 in an amount to provide about 1.5-1% by weight of fluoride ion.

The wax content of liquid 19 may be varied over wide ranges and it is only necessary that a sufficient amount be applied to result in a wax coating of sufficient thickness on the textile material 10. Usually the wax content of liquid 19 is about 5-75% by weight, and preferably about 20-50% by weight when it is a solution or emulsion. However, higher or lower concentrations of wax may be employed when desired. Alternatively, wax concentrations and waxing techniques may be used in accordance with prior art practices for waxing dental textile materials. It is not always necessary that the dental textile material be passed through a bath of liquid 19. For example, the wax coating may be applied by feeding the liquid 10 to metering rolls and passing the textile material 10 therebetween, or the liquid 19 may be used to saturate felt applicators which are in turn used to saturate the dental textile material 10 when it is passed therebetween.

In instances where liquid 19 is a solution of the wax in a volatile solvent, then preferably the dryer-cooler 24 is operated at a sufficiently high temperature to result in the rapid evaporation of the solvent content shortly after the satuarted textile material 10 has entered via opening 22 and prior to withdrawal via opening 35. Similarly, when the liquid 19 is an aqueous emulsion of wax, then the dryer-cooler 24 may be operated at an elevated temperature which results in the rapid evaporation of the water content of the emulsion, such as at about 150°–250° F. and preferably about 200°–225° F. In instances where the liquid 19 is molten wax, then the dryer-cooler 24 may be operated at a sufficiently low temperature to result in the rapid cooling of the wax coating below its solidification temperature. For instance, the dryer-cooler 24 may be maintained at a temperature of approximately 10°–100° F. below the solidification temperature of the wax by means of cool air passed thereto from cooler-blower 45.

Preferably, the wax containing liquid 19 which is on the textile material 10 as it emerges from the tank 14 is solidified as rapidly as possible so as to result in a substantially uniform distribution of the fluorine compound within the solid wax coating. This may be accomplished by flash drying in instances where the liquid 19 is an emulsion or solution of wax and in flash solidification in instances where the liquid 19 is molten wax.

The resultant wax coated dental textile material 10 may be used following prior art practices for the removal of food deposits from the teeth and gingiva. It is only necessary that the dental textile material of the present invention be substituted for that normally used for this purpose. The intimate contact between the waxed dental textile material and the teeth and gingiva results in the deposition of a therapeutic amount of the fluoride compound on the teeth which in turn inhibits the formation of dental caries. Frictional heat is often generated in instances where the dental tape is pulled vigorously over the teeth, and especially between the teeth at points of contact, and in such instances the therapeutic effects of the floride ion that is released is pronounced. Additionally, particles of wax containing the fluoride compound are deposited on the teeth at the points of contact, and in the general area of the gingiva, and slowly release fluoride ion over a substantial period of time. The therapeutic effects of the fluorine-containing compound are surprisingly pronounced and dental caries are reduced very markedly.

Any suitable fluorine-containing compound may be used in practicing the present invention provided it releases a therapeutic amount of fluoride ion to inhibit the formation of dental caries when the waxed dental textile material is intimately contacted with the teeth and gingiva to remove food deposits. Examples of fluorine compounds which releases fluoride ion under such conditions include sodium fluoride, potassium fluoride, ammonium acid fluoride, iron fluoride, stannic fluoride and stannous fluoride. Stannous fluoride is usually much preferred over the remaining fluorides.

The foregoing detailed description and the following specific examples are for purposes of illustration only, and are not limiting to the spirit or scope of the appended claims.

EXAMPLE I

Paraffin wax is dissolved in dry petroleum benzine having a distillation range of 35°–80° C. and a temperature of 30° C until a viscous solution is produced. Then dry powdered stannous fluoride in a very finely divided condition is dispersed in the viscous solution with vigorous agitation in an amount of 20 % based upon the weight of the paraffin wax to thereby produce a uniform suspension.

The resulting wax solution is charged to a glass lined tank provided with submerged glass coated rolls similar to that illustrated in the drawing. Uncoated multi-strand nylon dental floss of indefinite length is withdrawn from a master supply spool and passed under the submerged rolls and through the wax solution. Thereafter, the saturated nylon dental floss having a coating of the wax solution thereon is withdrawn from the tank and passed through a dryer. The dryer is operated at a temperature of about 85° C. Hot air is passed through the dryer and the solvent content of the wax solution is flash evaporated to thereby produce a solidified wax coating on the nylon dental floss containing the suspended stannous fluoride particles uniformly dispersed therein. The hot air is passed through the dryer in sufficient volume to dilute the petroleum benzin vapors sufficiently to avoid explosion and/or fire hazards.

The resultant waxed nylon dental floss having a solid wax coating thereon is withdrawn from the dryer and wound on small consumer type dental floss spools using a photoelectric counter and measuring device to assure that each spool received the desired length of dental floss. The filled spools of dental floss are packaged and stored awaiting use.

Microscopic examination of the dental floss shows that the wax coating contains the finely divided particles of stannous fluoride substantially uniformly dispersed therein. Upon testing the wax coated dental floss for removing food particles and deposits from the teeth and gingiva, it is noted that small particles of the wax coating are deposited at points of contact with the teeth. Thus the water insoluble wax particles are available for slowly releasing fluoride ion over a substantial period of time. The small initially exposed particles of stannous fluoride in the wax coating also dissolve in the saliva and tissue fluids to thereby release fluoride ion more rapidly but over a shorter period of time. Thus, the wax coating provides two types of fluoride treatment for the teeth.

EXAMPLE II

This example illustrates the application of a fluorine-containing wax coating from an aqueous emulsion of wax.

An aqueous emulsion containing 25 parts by weight of microcrystalline wax, 5 parts by weight of a nonionic synthetic detergent, and the remainder water is prepared following conventional prior art procedures. The wax is melted and then slowly added to water containing the nonionic surfactant with vigorous agitation. Thereafter stannous fluoride is dissolved in the aqueous emulsion in an amount of about 1.5–2% based upon the weight of the wax.

The wax emulsion is charged to a glass lined tank fitted with glass coated steel guide rolls similar in configuration to that illustrated in the drawing. Uncoated cotton dental floss is withdrawn from a master supply spool and passed under the guide rolls submerged in the aqueous emulsion of wax whereby the dental floss is saturated with the wax emulsion. The saturated dental floss is withdrawn from the aqueous emulsion, passed between felt wipers to remove excess emulsion, and then immediately passed through a dryer operated at a temperature of approximately 225° F. The water content of the aqueous emulsion saturating the dental floss is flash evaporated to thereby produce a solid wax coating on the dental floss which contains the stannous fluoride substantially uniformly dispersed therein. The dispersion is substantially uniform since the stannous fluoride is dissolved initially in the aqueous phase of the emulsion.

The resultant wax coated dental floss is thereafter packaged and tested following the general procedure outlined in Example I. Comparable results are obtained.

EXAMPLE III

This example illustrates the application of molten wax to dental floss.

Microcrystalline wax is heated until molten. Then very finely divided powdered stannous fluoride in an amount to provide 1.5 –2% by weight of fluoride ion is uniformly dispersed therein with vigorous agitation and with control of the temperature. A uniform viscous wax dispersion of stannous fluoride particles is achieved. The resultant molten wax is charged to a glass lined tank provided with submerged glass coated steel rolls similar to configuration to that illustrated in the drawing. Multistrand uncoated nylon dental floss is withdrawn from a supply spool and passed under the submerged guide rolls thereby impregnating the strands thereof with molten wax containing the suspended finely divided stannous fluoride particles. The molten wax bath is agitated to assure that the stannous fluoride particles remain uniformly dispersed therethrough.

The multistrand nylon dental floss impregnated with the molten wax is rapidly withdrawn from the tank and excess molten wax is removed by passing it between heated felt wipers. Thereafter the wax coating is rapidly solidified by passing the impregnated dental floss through a cooler supplied with a large volume of cool air having a temperature of approximately 10°–15° C. The molten wax coating solidifies almost immediately thereby retaining the finely divided particles of stannous fluoride substantially uniformly dispersed therethrough.

The wax coated dental floss thus produced is then packaged and tested following the general procedure of Example I. Comparable results are achieved.

EXAMPLE IV

This example illustrates the use of the wax coated dental products of the invention in the treatment of patients to inhibit the formation of dental caries.

The patients are divided into two groups and identified as group A and group B. Group A is further divided into three subgroups, i.e., subgroup A-1, subgroup A-2 and subgroup A-3. Subgroup A-1, A-2 and A-3 are given samples of the wax coated dental floss produced by experiments I, II and III, respectively, and instructed in the proper use thereof to remove food particles from the teeth and gingiva. Group B is similarly instructed but provided with conventional waxed dental floss which does not contain a fluorine compound.

The two groups are examined periodically at three month intervals and the rate of formation of dental caries is noted. The three subgroups using the waxed dental floss of the invention i.e., subgroups A-1, A-2, and A-3 have markedly fewer dental caries than the control Group B using the dental floss of the prior art which does not contain the fluorine compound. Thus, the waxed dental floss of the invention is effective in inhibiting the formation of dental caries.

When desired the tank 14 may be provided with conventional agitation means such as a propeller-type agitator for the purpose of maintaining the ingredients of liquid 19 uniformly suspended. The tank 14 also may be provided with conventional heating or cooling means for the purpose of maintaining the liquid 19 at a desired operating temperature. The prior art agitation means and heating or cooling means are not shown in the interest of simplifying the drawing.

I claim:

1. A method of preparing waxed dental textile material for use in removing food deposits from teeth and the gingiva comprising applying a coating of wax to dental textile material to thereby produce waxed dental textile material, the wax coating being water insoluble and solid at room temperature, the wax coating encompassing the dental textile material and having a fluorine-containing compound distributed therein which provides fluoride ion in a therapeutic amount of inhibit the formation of dental caries when the waxed dental textile material is intimately contacted with the teeth and gingiva to remove food deposits therefrom, the wax coating being applied in an amount whereby particles thereof are deposited on the teeth at the points of contact and in the general area of the gingiva and fluoride ion is slowly released therefrom over a substantial period of time, and the said fluorine-containing compound being present in the wax coating in an amount to provide about 0.0001–2% by weight of fluoride ion based upon the weight of the wax coating.

2. The method of claim 1 wherein the said fluorine-containing compound comprises stannous fluoride.

3. The method of claim 1 wherein the wax coating is applied by passing an elongated unwaxed dental textile material of indefinite length through a solution of wax in a volatile solvent, the textile material comprises a plurality of elongated generally longitudinally extending textile fibers and the textile fibers are coated with the wax solution, the fluorine-containing compound is present in the solution in an amount to provide about 0.001–10% by weight of fluoride ion, and the resultant dental textile material coated with the wax solution is passed through a drying zone and the solvent is evaporated therefrom to produce a coating of wax on the textile fibers which has the fluorine-containing compound substantially uniformly dispersed therein.

4. The method of claim 1 wherein the wax coating is applied by passing an elongated unwaxed dental textile material of indefinite length through an aqueous emulsion of wax, the textile material comprises a plurality of elongated generally longitudinally extending textile fibers and the textile fibers are coated with the wax emulsion, the fluorine-containing compound is present in the aqueous emulsion in an amount to provide about 0.001–10% by weight of fluoride ion, and the resultant dental textile material coated with the aqueous wax emulsion is passed through a drying zone and the water is evaporated therefrom to produce a wax coating on the textile fibers which has the fluorine-containing compound substantially uniformly distributed therein.

5. The method of claim 1 wherein the wax coating is applied by coating an elongated unwaxed dental textile material of indefinite length with molten wax, the dental textile material comprises a plurality of elongated generally longitudinally extending textile fibers and the textile fibers are coated with the molten wax, the fluorine-containing compound is substantialy uniformly distributed in the molten wax in an amount to provide about 0.0001–2% by weight of fluoride ion, and the resultant dental textile material coated with the molten wax is passed through a cooling zone and the temperature is reduced below the melting point of the wax to thereby produce waxed dental textile material having the fluorine-containing compound substantially uniformly distributed through the wax coating.

6. An elongated waxed dental textile material for use in removing food deposits from teeth and the gingiva comprising a plurality of elongated generally longitudinally extending textile fibers coated with a wax coating, the wax coating being water insoluble and solid at room temperature, the wax coating encompassing the dental textile material and having a fluorine-containing compound substantially uniformly distributed therein which provides fluoride ion in a therapeutic amount to inhibit the formation of dental caries when the waxed dental textile material is intimately contacted with the teeth and gingiva to remove food deposits therefrom, the wax coating being applied in an amount whereby particles thereof are deposited on the teeth at the points of contact and in the general area of the gingiva and fluoride ion is slowly released therefrom over a substantial period of time, and the said fluorine-containing compound being present in an amount to provide about 0.0001–2% by weight of fluoride ion based upon the weight of the wax coating.

7. The waxed dental textile material of claim 6 wherein the fluorine-containing compound comprises stannous fluoride.

8. The waxed dental textile material of claim 6 wherein the fluorine-containing compound is stannous fluoride and the stannous fluoride is present in the wax coating in an amount to provide about 1–1.5% by weight of fluoride ion based upon the weight of the wax coating.

9. The waxed dental textile material of claim 6 wherein the said textile fibers comprise a plurality of nylon filaments.

10. A method of inhibiting the formation of dental caries in teeth comprising cleaning the teeth at periodic intervals with an elongated waxed dental textile material to remove food deposits from the teeth and the gingiva, the dental textile material comprising a plurality of elongated generally longitudinally extending textile fibers and the textile fibers being coated with wax, the wax coating being water insoluble and solid at room temperature, the wax coating encompassing the dental textile material and having a fluorine-containing compound substantially uniformly distributed therein which provides fluoride ion in a therapeutic amount to inhibit the formation of dental caries when the waxed dental textile material is intimately contacted with the teeth and gingiva to remove food deposits therefrom, the wax coating being applied in an amount whereby particles thereof are deposited on the teeth at the points of contact and in the general area of the gingiva and fluoride ion is slowly released therefrom over a substantial period of time, and the said fluorine-containing compound being present in an amount to provide about 0.0001–2% by weight of fluoride ion based upon the weight of the wax coating.

11. The method of claim 10 wherein the fluorine-containing compound is stannous fluoride.

12. The method of claim 10 wherein the said plurality of textile fibers comprises a plurality of nylon filaments.

* * * * *